US012555665B2

(12) United States Patent
Karney

(10) Patent No.: US 12,555,665 B2
(45) Date of Patent: Feb. 17, 2026

(54) HOME EXERCISE PLAN PREDICTION

(71) Applicant: CERNER INNOVATION, INC., North Kansas City, MO (US)

(72) Inventor: Gregory Karney, Ashaway, RI (US)

(73) Assignee: CERNER INNOVATION, INC., Kansas City, MO (US)

( * ) Notice: Subject to any disclaimer, the term of this patent is extended or adjusted under 35 U.S.C. 154(b) by 931 days.

(21) Appl. No.: 17/831,027

(22) Filed: Jun. 2, 2022

(65) Prior Publication Data

US 2023/0395229 A1 Dec. 7, 2023

(51) Int. Cl.

| | |
|---|---|
| ***G16H 20/30*** | (2018.01) |
| ***A61B 5/11*** | (2006.01) |
| ***G16H 40/67*** | (2018.01) |
| ***G16H 50/30*** | (2018.01) |

(52) U.S. Cl.

CPC ............ *G16H 20/30* (2018.01); *A61B 5/1118* (2013.01); *A61B 5/1128* (2013.01); *G16H 40/67* (2018.01); *G16H 50/30* (2018.01); *A61B 2505/09* (2013.01)

(58) Field of Classification Search

CPC ........ G16H 20/30; G16H 40/67; G16H 50/30; G16H 50/50; G16H 50/70; A61B 5/1118; A61B 5/1128; A61B 2505/09; A61B 5/7275

See application file for complete search history.

(56) References Cited

U.S. PATENT DOCUMENTS

| | | | |
|---|---|---|---|
| 2014/0100464 A1 | 4/2014 | Kaleal | |
| 2015/0037771 A1 | 2/2015 | Kaleal, III | |
| 2018/0330810 A1 | 11/2018 | Gamarnik | |
| 2020/0054931 A1* | 2/2020 | Martin | G06F 3/011 |
| 2021/0008413 A1 | 1/2021 | Asikainen | |
| 2021/0138304 A1 | 5/2021 | Mason et al. | |
| 2022/0157427 A1 | 5/2022 | Keeley | |

OTHER PUBLICATIONS

USPTO Office Action in Co-pending U.S. Appl. No. 17/831,020; issued May 12, 2025.

USPTO, Office Action from co-pending U.S. Appl. No. 17/831,030; issued May 9, 2025.

* cited by examiner

*Primary Examiner* — Pei Yong Weng

(74) *Attorney, Agent, or Firm* — Kraguljac Law Group LLC

(57) ABSTRACT

Systems, methods and computer readable media are provided for determining patient risk of participating in a physical therapy digital home exercise program. The patient risk is generated by one or more artificial intelligence/machine learning (AI/ML) models. Based on the patient risks compared to the benefits, one or more actions may be initiated to create or modify a digital home exercise program for a patient.

16 Claims, 9 Drawing Sheets

| Threshold | Score |
|---|---|
| high | 0.5 |
| low | 0.49 |

*FIG. 6*

HOME EXERCISE PLAN PREDICTION

BACKGROUND

Physical therapy is generally considered the most cost effective and safest treatment for musculoskeletal injuries. Insurers usually require conservative treatment, such as physical therapy, before authorizing surgery. Physical therapists utilize a wide variety of interventions. Most of the physical therapist's treatment time is spent examining and identifying physical impairments, producing a diagnosis, providing a prognosis, educating patients, prescribing exercises, reviewing exercises, and providing manual therapy (hands on). Typically, a patient travels to the physical therapist's office multiple times to treat impairments. The physical therapist progressively integrates greater challenges until full function is achieved. A physical therapist may prescribe a home exercise program for the patient to perform exercises at home when not visiting the physical therapist's office. Patient diagnosis, education, and prescribing of home exercise programs varies between physical therapists and are communicated verbally to the patient. A patient's progress is evaluated visually by the physical therapist when the patient returns to see the physical therapist in the office.

BRIEF DESCRIPTION OF THE DRAWINGS

The present invention is described in detail below with reference to the attached drawing figures, wherein:

FIG. 6 depicts the thresholds in accordance with an embodiment of the disclosure;

SUMMARY

Figure 1:
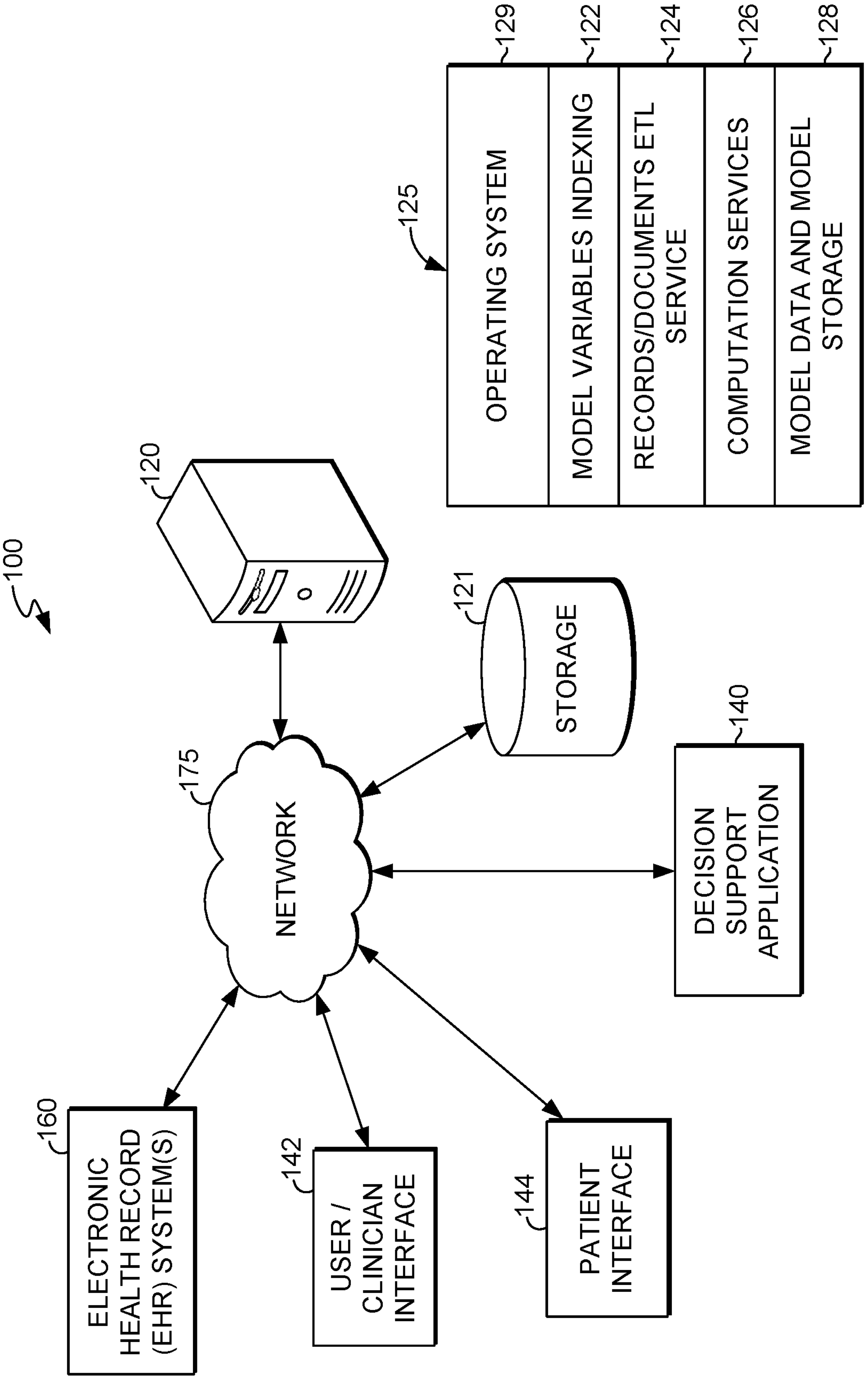
FIG. 1 depicts aspects of an illustrative operating environment suitable for practicing an embodiment of the disclosure.

Systems, methods, and computer readable media are provided changing a digital home exercise plan for a physical therapy patient. Input of a patient response to a physical therapy digital home exercise plan is received from a patient device. It is determined whether the input satisfies a threshold for changing the physical therapy digital home exercise plan for the patient. An action changing the physical therapy digital home exercise plan for the patient is initiated. Systems, methods, and computer readable media are provided for creating a digital home exercise plan for a physical therapy patient. Input of a patient impairment is received and satisfies a threshold for creating a physical therapy digital home exercise plan for the patient for the impairment. An action creating a physical therapy digital home exercise plan for the patient. Systems, methods, and computer readable media are provided changing a digital home exercise plan for a physical therapy patient. Input for physical therapy digital home exercise plan for a patient is received. A dataset of features from the input are extracted. At least one of the dataset of features from the input is utilized with a patient risk model to determine the input satisfies a threshold for changing the physical therapy digital home exercise plan for the patient. One or more changes are initiated to change the physical therapy digital home exercise plan for the patient.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different blocks or combinations of blocks similar to the ones described in this document, in conjunction with other present or future technologies. Moreover, although the terms "step" and/or "block" may be used herein to connote different elements of methods employed, the terms should not be interpreted as implying any particular order among or between various blocks herein disclosed unless and except when the order of individual blocks is explicitly described.

As one skilled in the art will appreciate, embodiments of the invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media, as discussed further with respect to FIGS. 1-2.

At a high level, this disclosure describes methods and devices for creating and modifying a digital home exercise plan prescribed by a licensed physical therapist. In implementations, the methods and devices allow for efficient prescription, administration, progression, and regression of a digital home exercise plan for a patient. This removes barriers, such as pain or complexity, to home exercise completion, and prevents patient excuses for not complying with a home exercise plan. Patient home exercise plan compliance may be tracked, authenticated and communicated to providers and payers. Consistent home exercise plan compliance improves patient healthcare outcomes substantially with conservative management, improves prognosis accuracy, and drives down the cost of care.

Implementations aim to accurately create and change a digital home exercise plan based on the predicted risk to the physical therapy patient. Further, continuous evaluation of input from a patient for a home exercise program increases the effectiveness of the home exercise program and reduces the likelihood of injury to the patient. The risk of changes to a home exercise plan for a patient are identified using the impairment diagnosis and patient input while executing the home exercise program. Utilizing these features to identify the risk of changes to a home exercise plan for a physical therapy patient allows for continuous virtual monitoring of the patient without visual monitoring by the physical therapist. After a home exercise program is digitally populated for the patient, patient input is received. The patient input may be queried so that feature values can be extracted and input into one or more machine learning models trained to predict the risk of making changes to the home exercise program for the patient. The models may be trained on data from patient data from a group of physical therapy patients. Prediction enables more effective progression and regression of exercises in a home exercise program for a patient without visual monitoring by a physical therapist. Based on the prediction, an intervening action, such as creating and modifying a home exercise program, is performed. One or more of these actions may be performed by automatically modifying computer code executed in a healthcare software program for treating the patient and/or care planning, thereby transforming the program at runtime. For example in one embodiment, the modification comprises modifying (or generating new) computer instructions (code) to be executed at runtime in the program, the modification may correspond to a creation or change in a home exercise program.

Further embodiments of the disclosure are directed to training one or more machine learning models to predict risk of making changes to a home exercise plan. Training the models may include identifying risk from reference data for physical therapy patients. Feature selection may be performed separately on models such that different features may be used from the reference data set.

Referring now to the drawings generally and, more specifically, referring to FIG. 1, an aspect of an operating environment 100 is provided suitable for practicing an embodiment of this disclosure. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data stores distributed across multiple locations). However, showing every variation of each item might obscure aspects of the invention. Thus, for readability, items are shown and referenced in the singular (while fully contemplating, where applicable, the plural). As shown in FIG. 1, example operating environment 100 provides an aspect of a computerized system for compiling and/or running an embodiment of a computer-decision support application for creating and modifying a home exercise plan. Environment 100 includes one or more electronic health record (EHR) systems 160, such as a hospital EHR system and/or physical therapy digital record, communicatively coupled to a network 175, which is communicatively coupled to a computer system 120. In some embodiments, components of environment 100 that are shown as distinct components may be embodied as part of or within other components of environment 100. For example, EHR systems 160 may comprise one or more EHR systems, such as hospital EHR systems, physical therapy records, health information exchange EHR systems, ambulatory clinic EHR systems, and/or cardiac EHR systems. Such EHR systems 160 may be implemented in computer system 120. Similarly, EHR system 160 may perform functions for two or more of the EHR systems (not shown).

Network 175 may comprise the Internet and/or one or more public networks; private networks; other communications networks, such as a cellular network; or similar network for facilitating communication among devices connected through the network. In some embodiments, the configuration of network 175 may be determined based on factors, such as the source and destination of the information communicated over network 175, the path between the source and destination, or the nature of the information. For example, intra-organization or internal communication may use a private network or virtual private network (VPN). Moreover, in some embodiments, items shown as being communicatively coupled to network 175 may be directly communicatively coupled to other items shown communicatively coupled to network 175. In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health and physical therapy records, which may be stored on storage 121, and may further include one or more computers or servers that facilitate the storing and retrieval of health records. In some embodiments, EHR system 160 may be implemented as a cloud-based platform or may be distributed across multiple physical locations. EHR system 160 may further include record systems that store real-time or near real-time patient (or user) information, such as information recorded from sensors on wearable, bedside, or in-home patient monitors and patient interface 144, for example. Although FIG. 1 depicts an exemplary EHR system 160 that may be used for storing patient information, it is contemplated that an embodiment may also rely on a decision support application 140 for storing and retrieving patient record information.

Example operating environment 100 further includes interface 142 and interface 144 communicatively coupled through network 175 to EHR system 160. Although environment 100 depicts an indirect communicative coupling between interface 142 and 144 and EHR system 160 through network 175, it is contemplated that one embodiment of interface 142 and 144 is communicatively coupled to EHR system 160 directly. An embodiment of user/clinician interface 142 and interface 144 takes the form of a graphical user interface operated by a software application or set of applications (e.g., decision support application 140) on a computing device. In an embodiment, the application includes the PowerChart® software manufactured by Cerner Corporation. In an embodiment, the application is a Web-based application or applet. User/clinician interface 142 and interface 144 facilitate accessing and receiving information from a user or physical therapist about a physical therapy patient or set of physical therapy patients for which the likelihood of risk in changing a home exercise plan is predicted according to the embodiments presented herein. Such information may include patient history; healthcare resource data; physiological variables (e.g., vital signs) measurements, time series, and predictions (including plotting or displaying the determined outcome and/or issuing an alert) described herein; or other health-related information, and facilitates the display of results, recommendations, or orders, for example. In an embodiment, user/clinician interface 142 and interface 144 also facilitate receiving orders, such as orders for more resources, from a user based on the results of predictions. Interfaces 142 and 144 may also be used for providing diagnostic services or evaluation of the performance of various embodiments.

An embodiment of decision support application 140 comprises a software application or set of applications, which may include programs, routines, functions, or computer-performed services, residing on a client computing device; on one or more servers in the cloud; or distributed in the cloud and on a client computing device, such as a personal computer, laptop, smartphone, tablet, mobile computing device, front-end terminals in communication with back-end computing systems, or other computing device(s) such as computer system 120 described below. In an embodiment, decision support application 140 includes a Web-based application or applet (or set of applications) usable to provide or manage user services provided by an embodiment of the invention. For example, in an embodiment, decision support application 140 facilitates processing, interpreting, accessing, storing, retrieving, and communicating information acquired from EHR system 160 or storage 121, including predictions and condition evaluations determined by embodiments of the invention as described herein. In an embodiment, decision support application 140 sends a recommendation or notification, such as an alarm or other indication, directly to user/clinician interface 142 and/or patient interface 144 through network 175. In an embodiment, decision support application 140 sends a maintenance indication to user/clinician interface 142. In some embodiments, decision support application 140 includes or is incorporated into a computerized decision support application, as described herein. Further, some embodiments of decision support application 140 utilize user/clinician interface 142 and/or patient interface 144. For instance, in one embodiment of decision support application 140, an interface component, such as user/clinician interface 142 and/or patient interface 144, may be used to facilitate access by a user, including a clinician or patient, to functions or information on a sensor device, such as operational settings or parameters, user identification, user data stored on the sensor device, for example.

In some embodiments, decision support application 140 utilizes interfaces 142 and 144 to facilitate accessing and receiving information from a user or clinician or patient according to the embodiments presented herein. Decision support application 140 and/or interfaces 142 and 144 also facilitate the display of results, recommendations, or orders, for example. In an embodiment, decision support application 140 also facilitates receiving orders, scheduling time with clinicians (including follow up visits), or queries from a user, based on the results of a predicted risk, which may utilize user/clinician interface 142 and/or interface 144 in some embodiments.

Example operating environment 100 further includes computer system 120, which may take the form of a server, which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations, such as one or more local clients and one or more remote servers, and may be distributed across the other components of example operating environment 100. For example, a portion of computer system 120 may be embodied on the computer system supporting decision support application 140. In one embodiment, computer system 120 comprises one or more computing devices, such as a server, desktop computer, laptop, or tablet, cloud-computing device or distributed computing architecture, a portable computing device, such as a laptop, tablet, ultra-mobile PC, or a mobile phone.

Embodiments of computer system 120 include computer software stack 125, which, in some embodiments, operates in the cloud as a distributed system on a virtualization layer within computer system 120, and includes operating system 129. Operating system 129 may be implemented as a platform in the cloud and is capable of hosting a number of services, such as services 122, 124, 126, and 128, described further herein. Some embodiments of operating system 129 comprise a distributed adaptive agent operating system. Embodiments of services 122, 124, 126, and 128 run as a local or distributed stack in the cloud, on one or more personal computers or servers, such as computer system 120, and/or a computing device running interfaces 142 and 144 and/or decision support application 140. In some embodiments, interfaces 142 and 144 and/or decision support application 140 operate in conjunction with software stack 125.

In embodiments, model variables indexing service 122 provide services that facilitate retrieving frequent item sets, extracting database records, and cleaning the values of variables in records. For example, service 122 may perform functions for synonymic discovery, indexing, or mapping variables in records, or mapping disparate health systems' ontologies. In some embodiments, model variables indexing service 122 may invoke computation services 126. Predictive models service 124 is generally responsible for providing one or more models for predicting risk of change to a home exercise plan as described in connection to decision support application 200 of FIG. 2 and/or methods 300, 800, and 900 of FIGS. 3, 8, and 9 respectively.

Computation services 126 perform statistical software operations, such as computing the transformed variable predictions, transferred features, such as log and log 1*p* functions of features, and severity or risk indices as described herein. In an embodiment, computation services 126 and predictive models service 124 include computer software services or computer program routines. Computation services 126 also may include natural language processing services (not shown), such as Discern nCode™ developed by Cerner Corporation, or similar services. In an embodiment, computation services 126 include the services or routines that may be embodied as one or more software agents or computer software routines. Computation services 126 also may include services or routines for using one or more models, including logistic regression models, for predicting patient risk.

In some embodiments, stack 125 includes file system or cloud-services 128. Some embodiments of file model data and model storage 128 may comprise an Apache Hadoop and Hbase framework or similar frameworks operable for providing a distributed file system and which, in some embodiments, provide access to cloud-based services, such as those provided by Cerner Healthe Intent®. Additionally, some embodiments of model data and model storage 128 or stack 125 may comprise one or more stream processing services (not shown). For example, such stream processing services may be embodied using IBM InfoSphere stream processing platform; Twitter Storm stream processing; Ptolemy or Kepler stream processing software; or similar complex event processing (CEP) platforms, frameworks, or services, which may include the use of multiple such stream processing services in parallel, serially, or operating independently. Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which, in some embodiments, includes patient data for a candidate or target patient (or information for multiple patients), including raw and processed patient data; digital input by a user or patient; variables associated with recommendations; recommendation knowledge base; recommendation rules; recommendation update statistics; an operational data store, which stores events, frequent itemsets (such as "X often happens with Y", for example) and itemsets index information; association rulebases; agent libraries, solvers, and solver libraries; and other similar information, including data and computer-usable instructions; patient-derived data; and healthcare provider information, for example. It is contemplated that the term "data" used herein includes any information that can be stored in a computer storage device or system, such as user-derived data, computer usable instructions, software applications, or other information. In some embodiments, storage 121 comprises data store(s) associated with EHR system 160. Further, although depicted as a single storage store, storage 121 may comprise one or more data stores, or may be in the cloud.

In some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system; a data processing system; a centralized computing system; a single computer, such as a desktop or laptop computer; or a networked computing system.

A licensed physical therapist creates a treatment plan for a physical therapy patient. A treatment plan for a physical therapy patient is a broad document that guides treatment of the patient. A physical therapy plan of care or treatment plan typically includes: the date the plan of care being sent for certification becomes effective, diagnoses, long term treatment goals, type, amount duration and frequency of therapy services, signature, date and professional identity of the physical therapist establishing the plan.

A licensed physical therapist has a state licensure designation for practicing as a physical therapist. Typically, a physical therapist has a degree in physical therapy and has passed the National Physical Therapy Exam administered by the Federation of State Boards of Physical Therapy. Using the treatment plan signed by the physical therapist as a guide, a patient is provided with a variety of therapeutic exercises to be performed both when visiting a physical therapist and when the patient is home. In implementations, a home exercise program provides individualized set of therapeutic exercises that a patient is taught by their physical therapist to be completed at home, to complement and reinforce their program in the clinic.

Historically, exercises for a home exercise plan are recommended verbally by a physical therapist for the patient to be performed between treatment sessions with the licensed physical therapist. The home exercise plan is usually performed first by the patient in the presence of the physical therapist to ensure proper technique is utilized. Conventionally, the technique performed by the patient is refined over multiple sessions and progressed or regressed by the physical therapist verbally during in-person session(s) based on the physical therapist's visual observation of the patient's response to each exercise.

Figure 2:
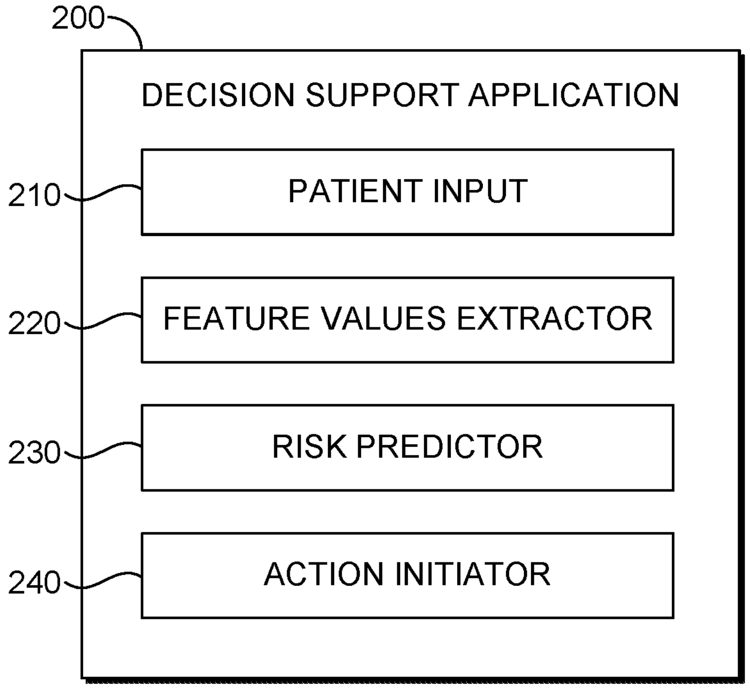
FIG. 2 depicts an example decision support application, in accordance with an embodiment of the disclosure.

FIG. 2 depicts an example embodiment of a decision support application 200 for reducing the physical therapy risk of patients. Decision support application 200 may be embodied as on one or more devices as shown in FIG. 1. In one embodiment, decision support application 200 may be integrated into a computing system that is part of a health care facility's (e.g., a hospital) and physical therapy computerized system as described with respect to the operating environment 100 of FIG. 1. Decision support application 200 includes a patient input identifier 210; a feature values extractor 220; a risk predictor 230; and an action initiator 240.

In implementations, device 200 receives digital input for a patient. The digital input may include general health indicators, including body mass index (BMI), blood pressure, height, weight, sex, and age. In implementations, digital input may include information about the patient's physical impairment and/or physical therapy outcome measure data, such as disabilities of the arm, shoulder, and hand (DASH), Oswestry low back pain questionnaire, and/or neck disability index. In implementations, digital input may include objective measurements from evaluation, such as range of motion impairments (goniometric measurements, strength, joint mobility impairments, balance deficits or outcome measures (BERG balance scale, Tinetti).

In implementations, the digital input for a patient is received from a digital record of patient information, such as an electronic medical record and/or physical therapy record. In implementations, the digital input for a patient is received from a physical therapy digital record for the patient entered by a licensed physical therapist to document evaluation, examination, and follow-up visits. Digital input for the patient may also be captured directly from digital devices such as cameras, 3d cameras, wearable sensors, smart phones, and applications that interact with a patient to capture digital input for the patient.

Among other things, methods, and systems for creating and changing a digital home exercise program by predicting the likelihood of risk for a physical therapy patient are provided. A digital home exercise plan is created by decision support application 200 under the authorization and/or approval of a licensed physical therapist treating a patient. In implementations, a physical therapist may provide pre-approval to allow decision support application 200 to create or modify a home exercise plan under the guidance of the treatment plan for the patient. In other implementations, decision support application 200 may provide suggestions to a physical therapist to create or modify a home exercise plan and receive approval from the physical therapist. In other implementations, decision support application 200, where legally permitted to do so, may create and modify the home exercise plan under the guidance of the treatment plan for the patient.

In exemplary embodiments, patient risk prediction is generated using one or more artificial intelligence/machine learning (AI/ML) models trained on data for a group of physical therapy patients having one or more physical impairments. Based on the patient risk prediction, one or more actions may be initiated. For instance, the patient risk prediction may trigger one or more actions to create or change a digital home exercise program for a patient. A digital home exercise plan design optimally challenges the patient without injury. The zone of difficulty for a patient is monitored digitally such that the digital home exercise plan is not too hard or too easy for the patient.

Implementations of the invention, allow for a home exercise plan to be created digitally for a patient. Feature values extractor 220 of decision support application 200 extracts variables from patient input 210, such as impairment, to create a digital home exercise plan for a patient. Utilizing the machine learning model described below, decision support application 200 populates one or more exercises for the home exercise program for the patient to address the impairment from patient input 210. Action initiator 240 of decision support application 200 initiates an action generating one or more exercises for digital home exercise programs for a variety of physical impairments. The exercises for the home exercise plan may be changed or edited by decision support application 200. The exercises populated for each impairment are based on consensus best practice for the treatment of each impairment. Impairments may include strength deficits, range of motion (ROM) deficits, joint mobility deficits, or neuro-muscular control deficits.

Risk predictor 230 of decision support application 200 grades impairments based on patient input 210 using a severity scale unique to the impairment type (ROM vs strength vs joint mobility) for generating exercises for the digital home exercise program for a patient. If risk predictor 230 determines the patient has a risk of a severe strength impairment based on patient input, the action initiator 240 generates one or more exercises, such as a gravity eliminated active movement, an active assisted movement, or an isometric contraction. Action initiator 240 generates one or more exercises of moderate difficulty for a risk of moderated impairment for the patient. Action initiator 240 generates one or more difficult exercises if the risk for the patient is determined to be a mild impairment. Decision support application 200 generates a chain of exercises progressions for the digital home exercise program for the patient. In implementations, the action initiator 240 may begin with an easy exercise for the impairment in the digital home exercise program, then progress towards more difficult exercises. Decision support application 200 has a corresponding exercises and progressions for each impairment generated by action initiator 240 depending on the prediction of risk predictor 230.

The digital home exercise plan for the patient generated by action initiator 240 is accessible to the patient at home by patient interface 144. In implementations, action initiator 240 provides the patient with information so the patient can practice the digital home exercise program correctly. Action initiator 240 may provide examples and video guided exercises via patient interface 144 both while the patient is at home and in implementations while the patient is in-person with the physical therapist.

The decision support application 200 is also developed to predict risk of changing a digital home exercise program for a patient, to ensure timely intervention, and prevent injury while allowing the patient to continue to progress. Additionally, action initiator 240 may output meaningful features that impact patient risk. The risk predictor 230 determines whether there is an increase or decrease risk of changing a digital home exercise plan for a patient.

Action initiator 240 helps progress a patient through a physical therapy home exercise plan in a safe and effective manner by updating patient interface 144 with a visual depiction of the patient's progress made thus far and a predictive rate of future progress. The visual depiction provides patient objectives and allows the patient to model different frequencies of home exercise plan completion to help the patient make informed decisions when executing the home exercise plan.

Risk predictor 230 may also determine when significant deviations occur from the predicted models in patient execution of a home exercise plan. Significant deviations may indicate a more serious condition, such as cancer, multiple sclerosis, Parkinson's disease or other serious conditions. Risk predictor 230 facilitates early detection of serious conditions during treatment. Action initiator 240 provides patient interface 144 and/or clinician interface 142 with visual updates throughout treatment, alerting the patient and provider or significant deviations and allowing expedited specialist referral when significant deviations occur from the predicted models. Based on the risk prediction, action initiator 240 may automatically schedule a patient examination with a specialist via an EHR.

Patient input 210 is received by decision support application 200 and feature values are extracted by feature values extractor 220 when the patient is performing exercises outside of the in-person physical therapy session. In implementations, patient input comes from cameras, 3d cameras, wearable sensors, smart phones, and patient interface 144 that interacts with a patient to capture patient input. A variety of video analyzers may be utilized to interpret patient movements and motions in the video input. Video motion analysis obtains data and information about moving objects from video. Data may include speed and acceleration calculations, task performance analysis, and distance calculations. In implementations, methodologies for analyzing movements and motions in from photos or videos may include strobographic image analysis and dynamic geometry software applications. In other implementations, sensors, attached to the patient, to sense data about motion, acceleration, posture, joint torque, balance and other mechanical measurements of a patient's body and movement. The data from the sensors is analyzed for features that indicate whether f patient to perform a cost benefit analysis of changing a home exercise plan for a patient.

Patient interface 144 communicates with decision support application 200 with information of how tissues are responding to exercises in the digital home exercise program. Action initiator 240 may provide patient interface 144 with tutorials and instructions regarding pain while performing the exercises of the digital home exercise plan. In implementations, patient interface 144 receives input of patient pain or lack thereof, and where/what kind of pain the patient is experiencing when performing the exercises of the digital home exercise plan. Patient interface 144 prompts the patient to grade the pain and difficulty during and/or after patient performs the exercise of the digital home exercise plan. Action initiator 240 adjusts exercise progression of a digital home exercise program based on the patient's response and risks determined by risk predictor 230. One or more of these actions may be performed by automatically modifying computer code executed in a healthcare software program for treating the patient and/or care planning, thereby transforming the program at runtime. For example in one embodiment, the modification comprises modifying (or generating new) computer instructions (code) to be executed at runtime in the program, the modification may correspond to a creation or change in a home exercise program.

Feature values extractor 220 extracts key values from the patient input, such as patient is not experiencing pain when performing an exercise. Risk predictor 230 utilizes the machine learning model described below to determine whether the patient meets the threshold for being low risk compared to benefits to progress the exercises in the digital home exercise program. Risk predictor 230 may determine that the value for patient input is higher than the normative value and determine the patient is low risk for injury if the digital home exercise program is progressed.

Action initiator 240 initiates a change to the digital home exercise program based on the risk determined by risk predictor 230 that a patient is low risk to progress the digital home exercise program. Action initiator 240 initiates a change to the digital home exercise program, progressing the patient to more difficult exercises by changing the exercise technique, exercise speed, rest duration, and/or repetition quantity.

In implementations, risk predictor 230 performs a cost benefit analysis assessing the risk of the patient performing the therapeutic exercise(s) of the digital home exercise program versus the benefit of the patient performing the therapeutic exercise(s). In implementations, feature value extractor 220 may extract input that the patient is in pain when performing an exercise. Utilizing the ML model, risk predictor 230 determines there is a high risk of injury to the patient due to the pain of performing the therapeutic exercise(s) compared to the benefits of the therapeutic exercise(s). In implementations, the risk of injury is weighted heavier than the patient benefit. Action initiator 240 generates and communicates a notification for the patient to stop the exercise. Action initiator 240 initiates a change to the digital home exercise program, regressing the patient to easier exercises by changing the exercise technique, exercise speed, rest duration, and/or repetition quantity.

In other implementations, value extractor 220 may extract input that the patient is not experiencing any pain when performing exercises. Utilizing the ML model, risk predictor 230 determines the benefits to the patient performing the therapeutic exercise(s) outweigh the risk of injury. Action initiator 240 generates and communicates a notification for the patient to continue the exercise. In implementations, if the patient has been performing the exercise without pain for a period of time, the risk predictor may determine that the benefits of progressing the exercises outweigh the risk to the patient. Action initiator 240 initiates a change to the digital home exercise program, progressing the patient to more difficult exercises by changing the exercise technique, exercise speed, rest duration, and/or repetition quantity.

In implementations, action initiator 240 provides the patient with information so the patient can perform the progressing or regressing changes to the digital home exercise program correctly. Action initiator 240 may provide examples and video guided exercises via patient interface 144. Decision support application 200 may also monitor patient compliance with a digital home exercise program. In implementations, patient interface 144 does not receive input or receives limited input from the patient. Feature values extractor 220 extracts the input or lack of input. Risk predictor 230 determines that the patient is non-compliant with their digital home exercise program based on limited patient input or no input and is at high risk. Action initiator 240 may regress the exercises for the patient and/or reschedule in-person appointments with the physical therapist until risk predictor 230 determines the patient is being compliant with the digital home exercise program. The goal is to improve digital home exercise program compliance and improve the rate of successful patient outcomes. Improved patient compliance reduces the number of surgical interventions needed and the cost of treatment.

Decision support application 200 estimates the time until certain digital home exercise plan milestones are reached by a patient or until complete return of function is achieved. Milestones may vary by patient and may be defined by the patient in the digital home exercise plan. For example, a patient milestone may be to run five miles, while other patient milestones may be undisturbed sleep or washing hair and getting dressed without assistance.

The digital home exercise plan for the patient utilizes machine learning to populate the home exercise plan path for a patient depending on the goals of the patient and defined milestones. Using patient interface 144, patient milestones, digital home exercise plan, and estimated length of home exercise plan may be viewed by patient. In one implementation, patient milestone of getting dressed without pain is three weeks of completing exercises for the digital home exercise plan five times per week. Depending on patient compliance with the digital home exercise plan, the patient milestone may be completed in +/−one week from the estimated three weeks. The patient interface 144 is interactive and may be adjusted to see when different milestones are likely to be met and see how many times a patient may need to complete their exercises before each milestone will be met. Highly motivated and compliant patients may want to perform a home exercise program three times per day to hasten recovery and decrease the time for meeting milestones.

Figure 3:
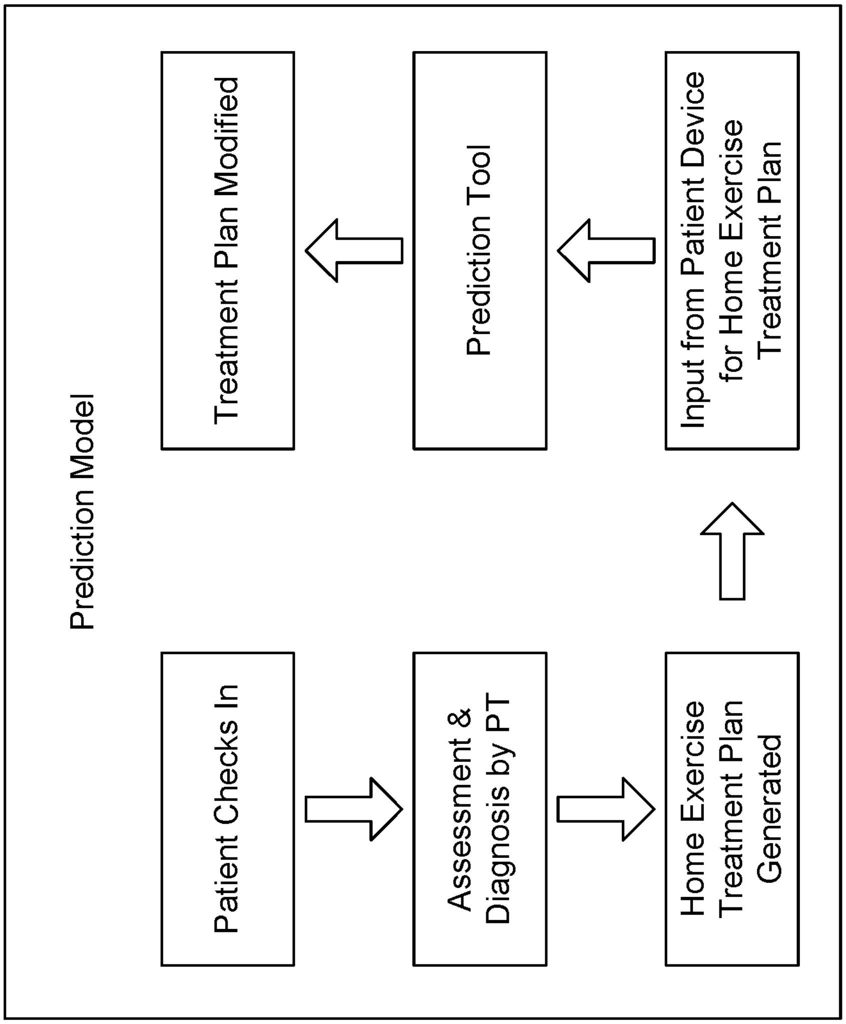
FIG. 3 depicts an aspect of physical therapy treatment model according to embodiments of the disclosure.

FIG. 3 depicts the patient risk prediction model in a digital physical therapy home exercise plan workflow. Identity input of a patient is received by decision support application 200. An assessment and diagnosis of one or more impairments input is received by decision support application 200. A digital home exercise program is generated by decision support application 200 based on the impairment received for the patient. Additional input is received from the patient while completing the digital home exercise program. The risk predictor 230 of decision support application 200 utilizes the impairment and machine learning to determine one or more modifications to the digital home exercise program for the patient.

Figure 4:
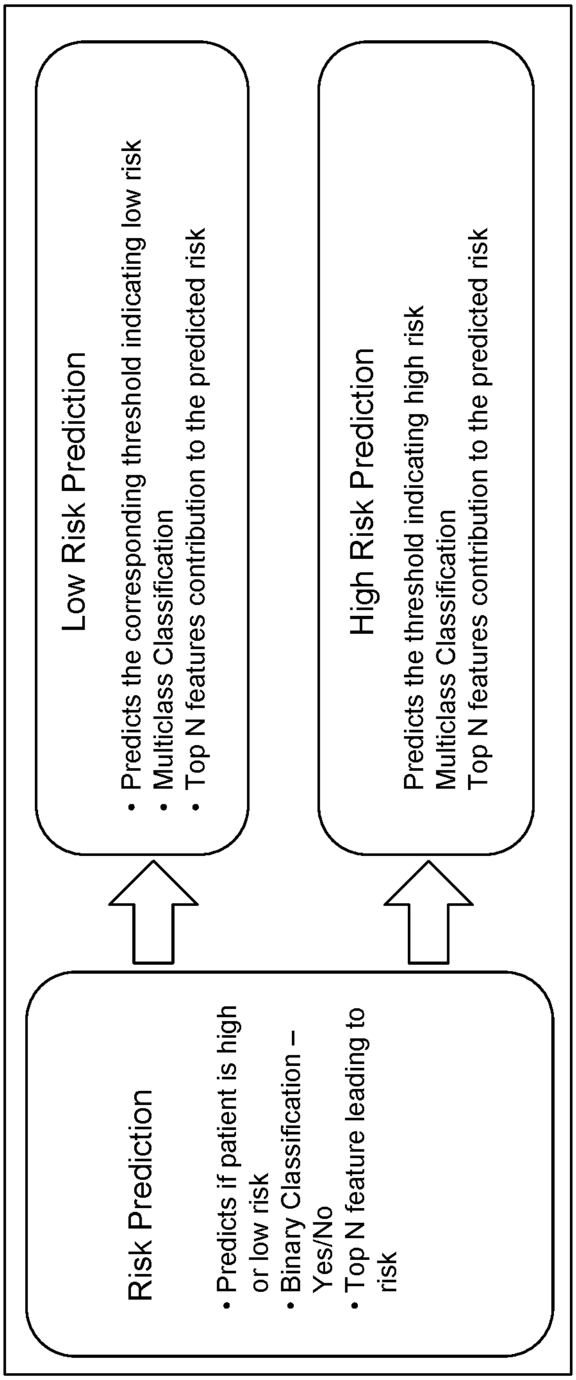
FIG. 4 depicts the risk prediction model in the physical therapy treatment process according to embodiments of the disclosure.

With reference to FIG. 4, an implementation of a high-level methodology for solving the problem of creating and modifying a digital home exercise program based on patient risk is shown. The patient risk of creating and modifying a digital home exercise program is solved as a classification problem that prepares data for the risk model. A classification problem organizes and formats the data. This step involves knowing the data source and development platform, data creation, data cleaning, and data transformation followed by feature engineering. Both binary and multi-class classification is used in various stages of the machine learning pipeline. Further, a sequential process is followed as shown in FIG. 4.

To develop the patient risk model, patient data for a group of physical therapy patients is provided, then converted to extensible markup language (XML) format, and further into a pandas data frame. Patient data is mapped to one or more physical impairments. Standard input features or dependent variables are created for capturing the various factors affecting the risk versus benefit of a home exercise program. A parsimonious set of features that capture the most meaningful information about patient risk using a home exercise program are chosen for the feature selection.

In implementations, the optimal combination of parameters is selected using hyperparameter tuning with the Bayesian optimization method to minimize the loss function and train the model with the best performance. The patient risk model is trained using an algorithm with the final set of features and the best parameters returned from hyperparameter tuning.

Figure 5:
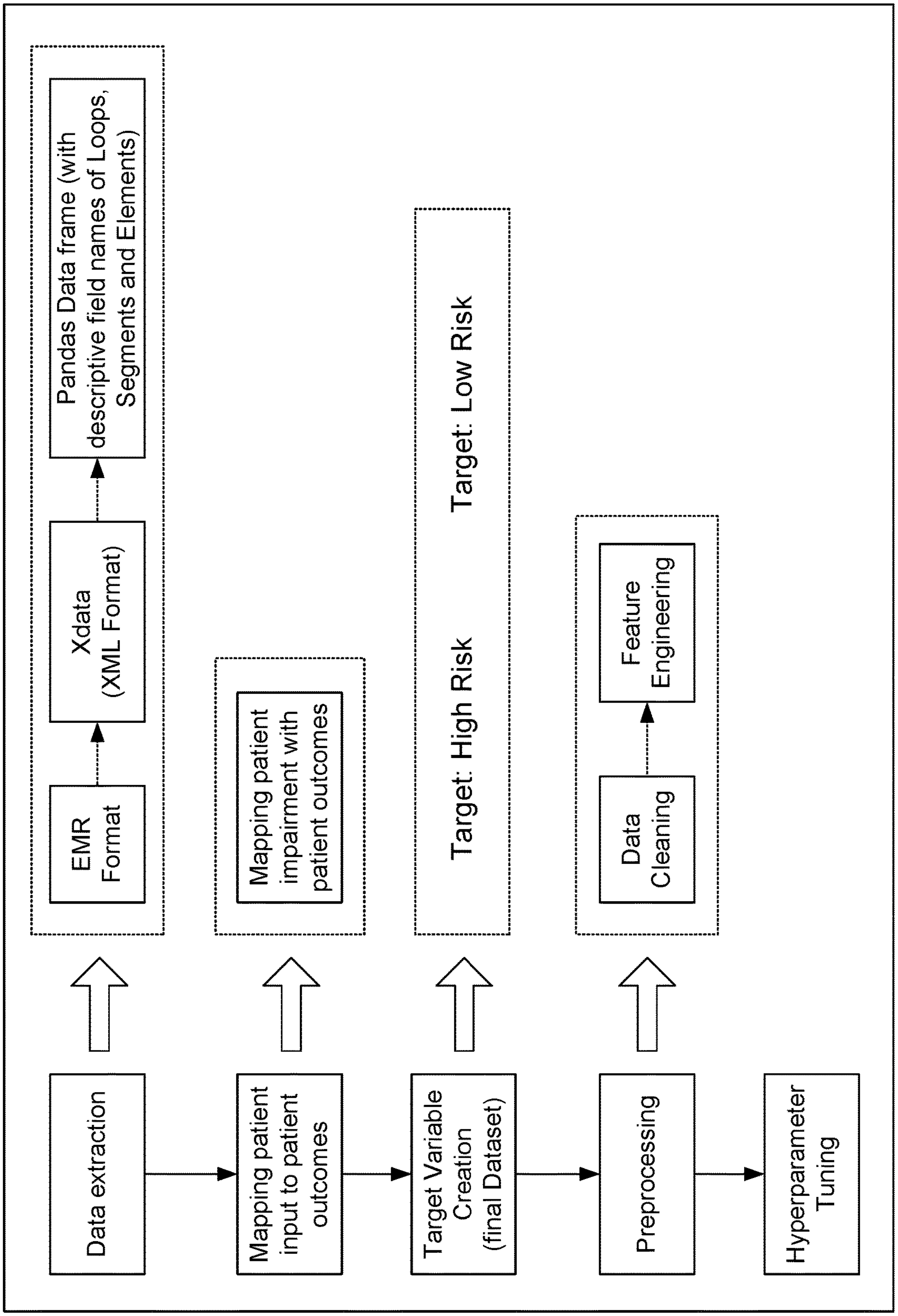
FIG. 5 depicts a flow diagram of a risk prediction model development in accordance with an embodiment of the disclosure.

As shown in FIG. 5, aspects of the present invention relate to a patient risk model for creating and modifying a digital home exercise program using machine learning techniques by predicting the likelihood of patient risk.

Feature Selection

A parsimonious set of features that capture the most meaningful information about home exercise programs and risk predictions and generalizes well on unseen data are extracted and used for feature selection. Data for a group of physical therapy patients is refined and mapped to exercise progressions for home exercise programs such that trends and patterns can be extracted. Patterns include the typical rate of recovery for an isolated impairment or a cluster of impairments for people with similar demographics and comorbidities. As different exercises may be used to address the same impairment, objective measures and outcomes are measured throughout the course of treatment to determine if one exercise is superior to another. This information will be used to refine the generated exercises and capture the most meaningful information about home exercise programs, risk predictions, and exercise progressions. In implementations, meaningful information about superior home exercises for an impairment may be based on clinician experience and external evidence based on Electromyography (EMG) studies. EMG studies may reveal exercises that elicit maximal muscle contraction, and more contraction typically yields faster recovery. An exercise, impairment, and outcome are mapped. Outcomes between exercises for the same impairment are mapped and exercises generated by decision support application 200 are adjusted accordingly.

In implementations, meaningful information about number of repetitions, resistance, rest break, warm-up, or exercise for an impairment is learned by capturing trends and patterns. The optimal blend of the variables is defined by machine learning to refine the optimal sets/reps/rest/ROM based on patient outcomes from the data from a group of physical therapy patients.

With reference to FIG. 5, the patient risk model is trained with the final set of features and the best parameters returned from hyperparameter tuning for each model respectively. Data is prepared for the patient risk model. A classification project organizes and formats the data. This step involves knowing the data source and development platform, data creation, data cleaning, and data transformation and, in some implementations, features engineering.

The patient risk model is solved as a classification problem. Both binary and multi-class classification is used in various stages of the ML pipeline. Sequential models are built using the hierarchical modeling concept of having a local classifier per parent node and at the end combined using joint probability. The conditional probability of an event B is the probability the event will occur given the knowledge that an event A has already occurred.

To get a better sense of how this model could be used in a real-world scenario, thresholds are provided based on the model performance. If the model was used with that threshold, assigning all episodes below that threshold as "low risk" and all those above the threshold as "high risk" as compared to benefits to the patient. FIG. 6 describes exemplary thresholds based on predictability score. The thresholds calculated by the high risk model may be used to determine which patients at "high risk" or "low risk" for injury as compared to benefits to the patient based on progressing an exercise of a home exercise plan for the patient.

The patient risk model is been deployed in a machine learning environment, such as the Cerner Machine Learning Environment (CMLE) platform. CMLE is a platform that leverages Amazon Web Services (AWS) to create an environment for direct interaction with the client data over the cloud. However, it will be appreciated that any MLE in a cloud hosted environment may be utilized.

Figure 7:
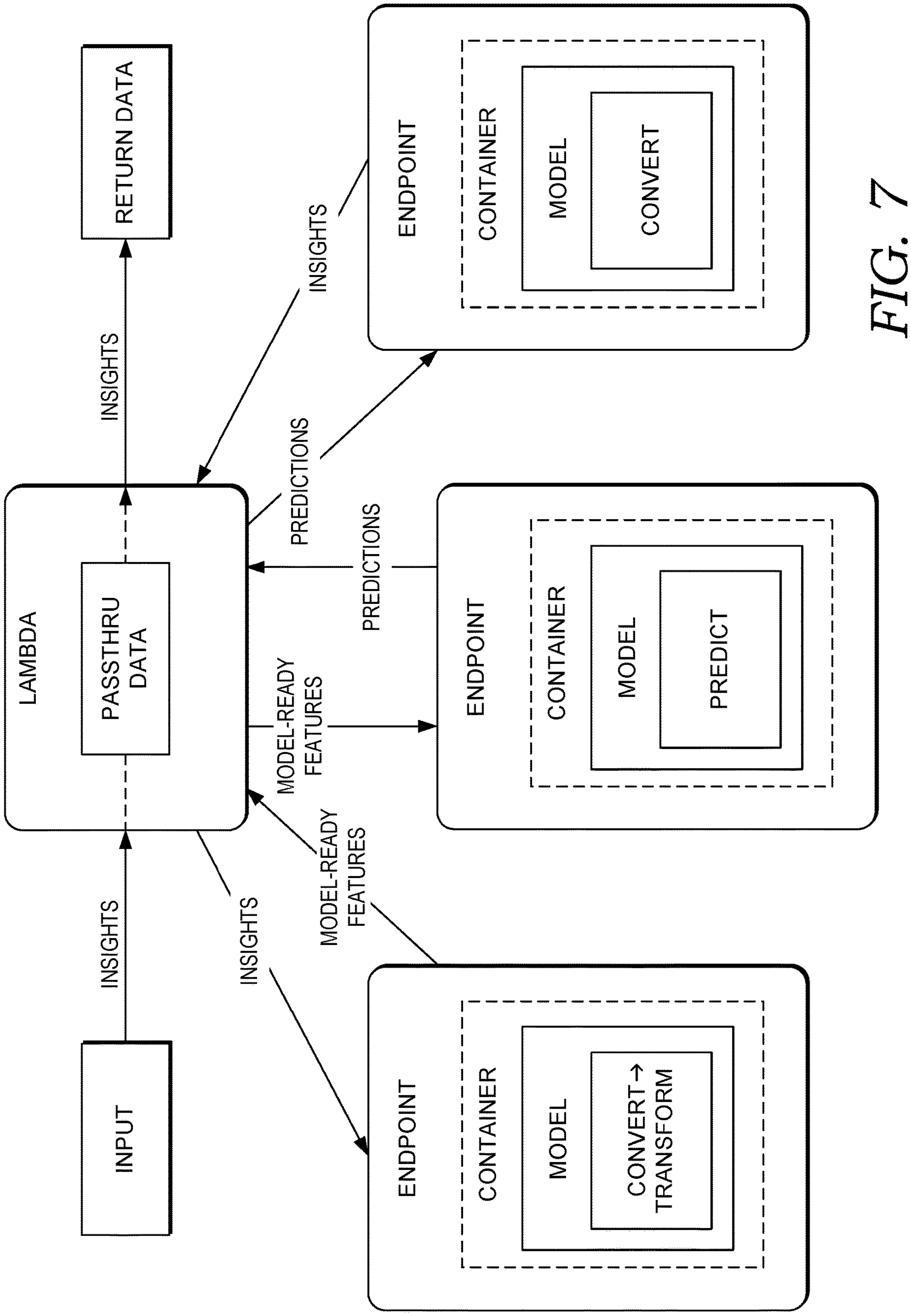
FIG. 7 depicts a flow diagram of the risk prediction model in accordance with an embodiment of the disclosure.

The patient risk model is consumed by the end-users via an application programming interface (API), which is hosted on the MLE platform. As shown in FIG. 7, input for physical therapy patients is converted into model-ready features for predictions. The entire prediction pipeline is divided into three SageMaker Endpoints (Transform, Predict, and Insights) with AWS Lambda as a controller. As specified in FIG. 7, SageMaker Endpoints is a service wrapper around a SageMaker Model.

Figure 8:
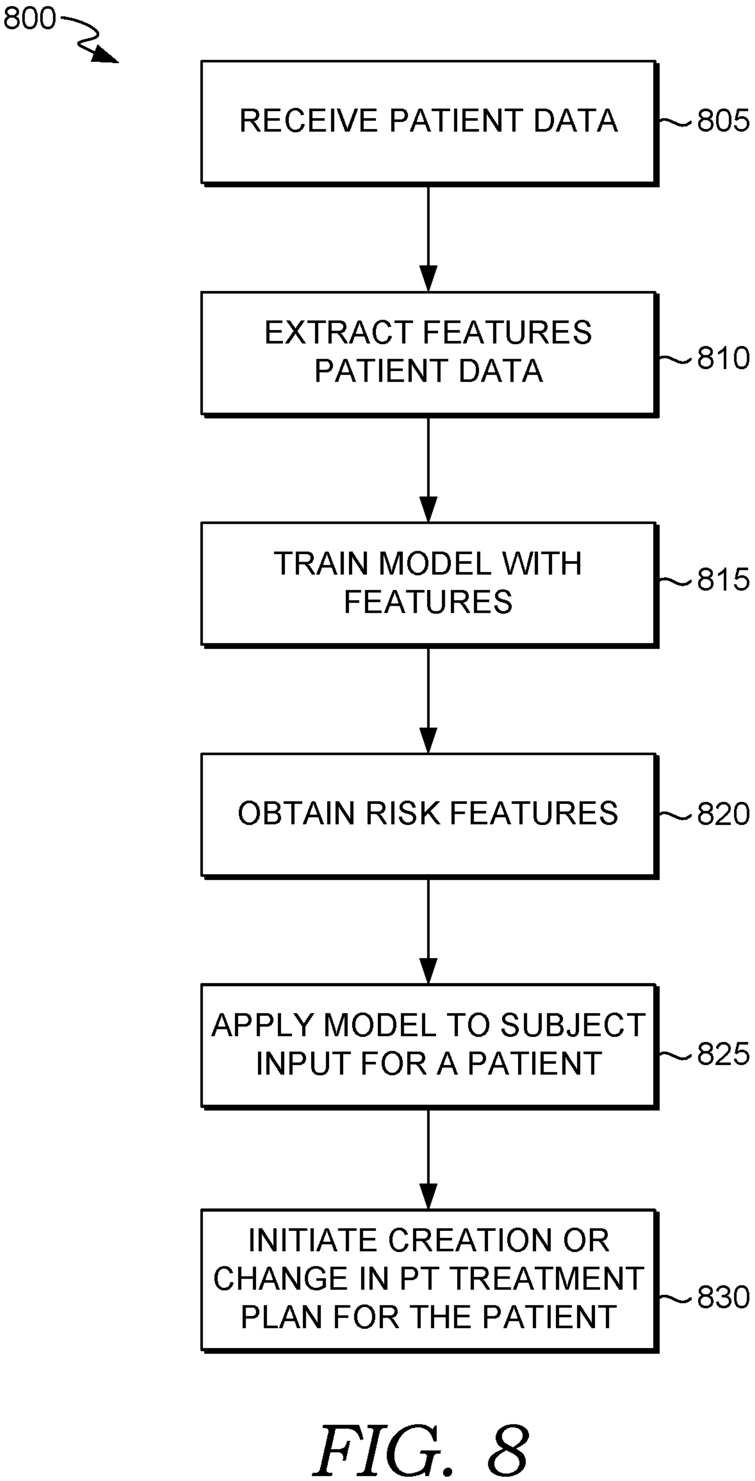
FIGS. 8 and 9 depict flow diagrams of methods for creating and/or modifying a home exercise plan in accordance with an embodiment of the disclosure.

With reference to FIG. 8, a method, system, and computer-readable media 800 are provided depicting a process for creating and modifying a digital home exercise plan for a patient based on patient risk. At 805, patient input from a plurality of patients is received by decision support application. In implementations, the patient data is extracted from the electronic medical records of a plurality of patients who have been prescribed a home exercise plan by a physical therapist for treating one or more impairments. An EMR database of historical patient data may be accessed for machine learning. At 810, the decision support model separates the patient data into features and determines a set of features that capture the most meaningful information about patient risk and benefits of using a home exercise program for physical impairments. At 815, the patient risk model is trained with the extracted features from the data from a plurality of patients.

At 820, after the patient risk model has been trained and deployed, patient input is received for a patient being treated by a physical therapist. The patient input is separated into different features for application of the patient risk model at 825. Based on the output from patient risk model, decision support application generates a digital home exercise program for the patient. In implementations, the digital home exercise program is generated using the patient risk based on the patient impairment and objective measurements from an evaluation, such as range of motion impairments (goniometric measurements, strength, joint mobility impairments, balance deficits or outcome measures (BERG balance scale, Tinetti).

At 825, the patient risk model trained at 815 is applied to the features of the patient input to generate a prediction of patient risk compared to patient benefits in creating or modifying a digital home exercise plan. At 830, the digital home exercise plan for the patient is generated or changed based on the outcome of risk from the patient risk model.

Figure 9:
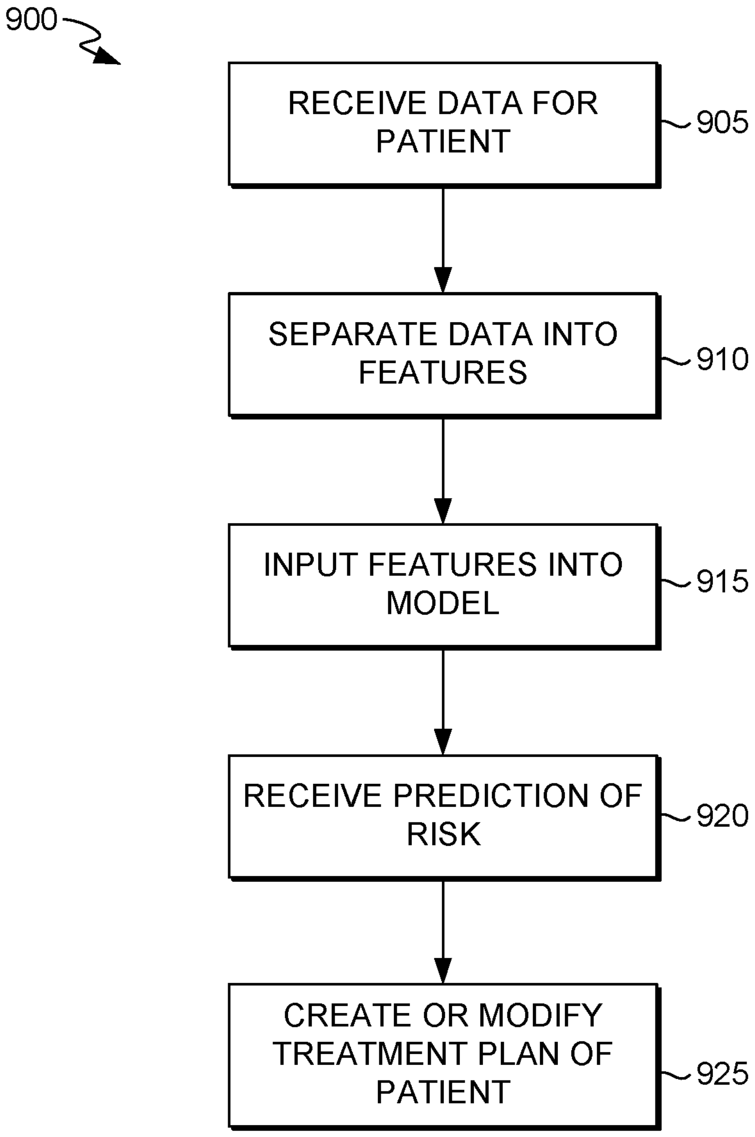

With reference to FIG. 9 a method, system, and computer-readable media 900 are provided depicting a process for creating and modifying a digital home exercise plan for a patient based on patient risk compared to patient benefits. At 905, patient input is received for a patient being treated by a physical therapist. The patient input may include impairment and objective measurements from evaluation. At 910, the patient input is separated into meaningful features determined by a patient risk model.

At 915, the meaningful features of the patient input are processed by the patient risk model at 920. Based on the output from patient risk model, at 925 the decision support application creates a digital home exercise program for the patient. In implementations, the digital home exercise program is created using the patient risk compared to patient benefits based on the patient impairment and objective measurements from an evaluation. In other implementations, at 925 a digital home exercise program for the patient is modified based on the patient risk compared to patient benefits.

What is claimed is:

1. A method performed by a computing system, the method comprising:

storing training data associated with a plurality of patients for training one or more machine learning models that include one or more models for generating a prediction of a need to change a physical therapy digital home exercise plan;

wherein the one or more machine learning models are trained with the training data, and the one or more machine learning models are trained to calculate a threshold to determine which patients are at high risk and low risk for injury as compared to benefits to the patients based on progressing an exercise;

receiving, by the computing system, digital input from a video camera capturing a patient performing exercises of the physical therapy digital home exercise plan;

extracting feature values from the digital input from the video camera;

based on the feature values extracted from digital input, generating the prediction of the need to change the physical therapy digital home exercise plan for the patient using the one or more machine learning models trained using the training data;

determining the prediction of the need to change the physical therapy digital home exercise plan is above the threshold; and initiating an action based on the prediction being above the threshold, wherein the action includes causing the video camera to discontinue capturing the digital input of the patient performing the exercises.

2. The method of claim 1, wherein the method further comprises:

executing, by the computing system, a software program that provides the physical therapy digital home exercise plan having a first configuration including at least an exercise technique, an exercise speed, and a rest duration; and in response to the prediction satisfying the threshold, automatically modifying computer code of the software program that changes the physical therapy digital home exercise plan at runtime to have a second configuration.

3. The method of claim 1, wherein extracting the feature values from the digital input from the video camera comprises extracting at least one objective feature comprising one or more of range of motion, strength, joint mobility impairments, and balance deficits.

4. The method of claim 1, wherein the prediction is above the threshold if the patient is at low risk for injury compared to benefits of changing the physical therapy digital home exercise plan.

5. The method of claim 1, wherein the action further includes generating computer instructions to change the physical therapy digital home exercise plan for the patient by increasing repetitions or range of motion exercises.

6. A non-transitory computer storage medium storing computer-usable instructions that, when executed by a processor of a computing system, cause the processor to perform a method in a computing system, the method comprising:

storing, at the computing system, training data associated with a plurality of patients for training one or more machine learning models that include one or more models for generating a prediction of a risk to change a physical therapy digital home exercise plan;

wherein the one or more machine learning models are trained with the training data to predict the risk to change, and the one or more machine learning models are trained to calculate a threshold to determine which patients are at high risk and low risk for injury as compared to benefits to the patient based on progressing an exercise;

receiving, by the computing system, digital input from a video camera capturing a patient performing exercises of the physical therapy digital home exercise plan;

extracting, by the processor, feature values from the digital input from the video camera;

based on the feature values extracted from digital input, generating, the prediction of the risk to change the physical therapy digital home exercise plan for the patient using the one or more machine learning models trained using the training data;

determining the prediction of the risk is above the threshold; and initiating, by the processor, an action based on the prediction being above the threshold, wherein the action includes causing the video camera to discontinue capturing the digital input of the patient performing the exercises.

7. The non-transitory computer storage medium of claim 6, further comprising instructions to cause the processor to:

execute a software program that provides the physical therapy digital home exercise plan having a first configuration including at least an exercise technique, an exercise speed, and a rest duration; and in response to the prediction satisfying the threshold, automatically modify computer code of the software program that changes the physical therapy digital home exercise plan at runtime to have a second configuration.

8. The non-transitory computer storage medium of claim 6, wherein extracting the feature values from the digital input from the video camera comprises extracting at least one objective feature comprising one or more of range of motion, strength, joint mobility impairments, and balance deficits.

9. The non-transitory computer storage medium of claim 6, wherein the prediction is above the threshold if the patient is at low risk for injury compared to benefits of creating the physical therapy digital home exercise plan.

10. The non-transitory computer storage medium of claim 6, further comprising receiving additional digital input that comprises at least one of physical therapy outcome measurement feature such as disabilities of an arm, a shoulder and a hand (DASH), Oswestry low back pain questionnaire, and a neck disability index.

11. A method in a computing system, the method comprising:

receiving, by the computing system, digital input from a video camera capturing a patient performing exercises of a physical therapy digital home exercise plan;

extracting feature values from the digital input from the video camera;

based on the feature values extracted from digital input, generating a prediction of a risk of injury to the patient performing the change a physical therapy digital home exercise plan using one or more machine learning models trained using training data;

determining the prediction of the risk of injury is above a threshold; and initiating an action based on the prediction being above the threshold, wherein the action includes causing the video camera to discontinue capturing the digital input of the patient performing the exercises.

12. The method of claim 11, further comprising:

accessing stored training data associated with a plurality of patients for training the one or more machine learning models that include one or more models for generating a prediction of a risk of injury to the patient performing a physical therapy digital home exercise plan.

13. The method of claim 11, wherein the physical therapy digital home exercise plan for the patient is authorized by a licensed physical therapist.

14. The method of claim 11, wherein extracting the feature values from the digital input from the video camera comprises extracting at least one objective feature comprising one or more of range of motion, strength, joint mobility impairments, and balance deficits.

15. The method of claim 11, wherein the prediction is above the threshold if the patient is at low risk for injury compared to benefits of changing the physical therapy digital home exercise plan.

16. The method of claim 13, wherein the action further includes generating computer instructions to change the physical therapy digital home exercise plan for the patient by increasing repetitions or range of motion exercises.

* * * * *